United States Patent [19]

Warriner

[11] Patent Number: Plant 6,092

[45] Date of Patent: Feb. 2, 1988

[54] ROSE PLANT JACTOP

[75] Inventor: William A. Warriner, Tustin, Calif.

[73] Assignee: Jackson & Perkins Company, Medford, Oreg.

[21] Appl. No.: 825,741

[22] Filed: Feb. 3, 1986

[51] Int. Cl.[4] ..... A01H 5/00

[52] U.S. Cl. ..... Plt./20

[58] Field of Search ..... Plt./20

*Primary Examiner*—Robert E. Bagwill

*Attorney, Agent, or Firm*—Manford R. Haxton

[57] ABSTRACT

A hybrid tea rose variety having dark green foliage contrasted with bright red flowers, a pleasant fragrance, high petal count and numerous stipulate glands on sepals and peduncles.

1 Drawing Figure

This present invention relates to a new and distinct variety of rose plant of the hybrid tea class which was originated by crossing the variety Grand Masterpiece, U.S. Plant Pat. No. 4,767, with an unnamed variety.

The primary objective of this breeding was to produce a new red hybrid tea rose variety exhibiting heavy production of large bright flowers. This objective was substantially achieved along with other desirable improvements as evidenced by the following unique combination of characteristics which are outstanding in the new variety and which distinguish it from its parents as well as from all other varieties of which I am aware:

1. Continuous production of large red flowers;
2. A high petal count;
3. Presence of numerous stipulate glands on sepals and peduncles;
4. Pleasant moderately scented flowers; and
5. Dark green leaves.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Grand Masterpiece, U.S. Plant Pat. No. 4,767.

*Pollen parent.*—Unnamed variety.

Classification:

*Botanical.*—Rosa hybrid.

*Commercial.*—Hybrid tea.

FLOWER

Observations made from specimens grown in a greenhouse at Irvine, Calif. in September, 1985.

Blooming habit: Continuous.

Bud:

*Size.*—1½"-2" when petals start to unfurl.

*Form.*—Long, pointed.

*Color.*—When sepals first divide, deep red (Red Group 46A); when half blown, upper side of petals, very bright red (Red Group 45A); lower side of petals Red Group 46B.

*Sepals.*—Color: Green Group 141C. Three appendaged sepals normally to heavily appendaged. Two unappendaged sepals hairy edge.

*Receptacle.*—Color: Green Group 141C. Shape: Funnel. Size: Small. Surface: Smooth.

*Peduncle.*—Length: Medium. Surface: Prickly and glandular. Color: Bronzy. Strength: Stiff.

Open bloom:

*Size.*—Large. Average open size 4"-4½".

*Borne.*—Singly to several together.

*Stems.*—Medium.

*Form.*—When first open, high center. Permanence: Retains its form to the end.

*Petalage.*—Number of petals under normal conditions: 45.

*Color.*—Center of flower: Upper side of petals, Red Group 45A; reverse side of petals, Red Group 46B. Base of petals, small yellow area. Major color: Red Group 45A.

*Variegations.*—Occasional white streak on an outside petal.

*Discoloration.*—General tonality at end of first day: None.

*Fragrance.*—Slight to moderate.

Petals:

*Texture.*—Thick.

*Shape.*—Obovate.

*Form.*—Tips slightly recurved.

*Arrangement.*—Imbricated.

*Persistence.*—Drop off cleanly.

*Lastingness.*—On the plant, long. As cut flower, long.

Reproductive parts:

*Anthers.*—Large. Color: Yellow. Arrangement: Regular around styles.

*Filaments.*—Color: Reddish.

*Pollen.*—Lemon yellow.

*Styles.*—Color: Reddish.

*Stigmas.*—Color: Yellow.

PLANT

Form: Bush.

Growth: Vigorous.

Foliage: Number of leaflets on normal mid-stem leaves: 5–7.

*Size.*—Large.

*Quantity.*—Normal.

*Color.*—New foliage: Reddish. Old foliage: Dark green (Green Group 137A).

Leaflets:

*Shape.*—Broadly oval.

*Texture.*—Smooth.

*Edge.*—Serrated.

*Serration.*—Double.

*Petiole.*—Rachis: Color: Reddish. Underside: Rough, with prickles and glands.

*Stipules.*—Medium, serrated.

*Disease resistance.*—Susceptible, under normal growing conditions at Irvine, Calif.

Wood:

*New wood.*—Color: Reddish. Bark: Smooth.

*Old wood.*—Color: Green. Bark: Smooth.

Prickles:

*Quantity.*—On main canes from base: Ordinary. On laterals from main canes: Ordinary.

*Form.*—Hooked downward.

*Color when young.*—Red.

Small prickles:

*Quantity.*—On main stalks, few. On laterals, many.

*Color.*—Reddish.

I claim:

1. A new and distinct variety of rose plant of the hybrid tea class substantially as herein shown and described characterized particularly as to novelty by the unique combination of dark green foliage contrasted with bright red flowers, a pleasant fragrance, high petal count and the presence of numerous stipulate glands on sepals and peduncles.

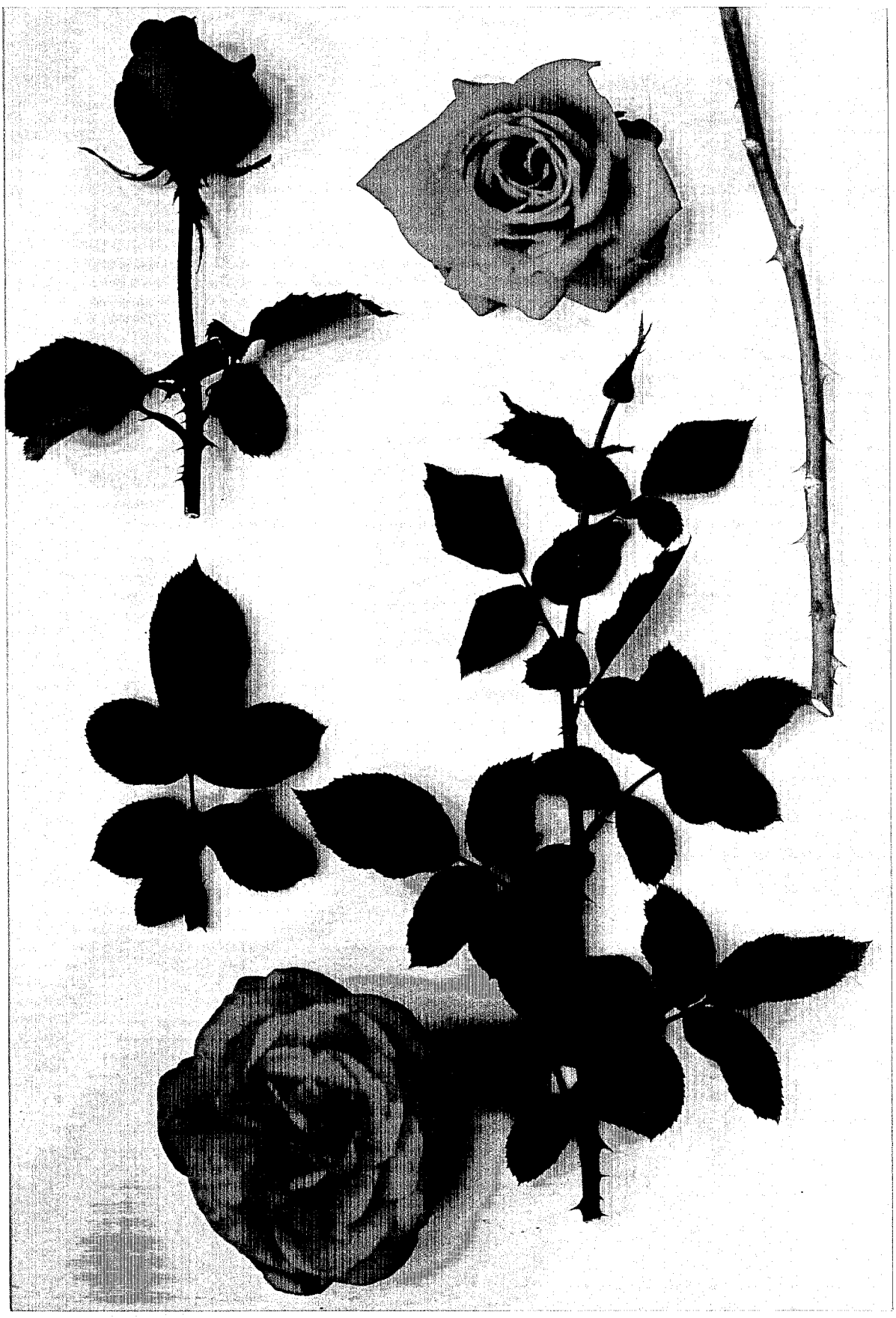

* * * * *